US006297357B1

(12) United States Patent
Giordano

(10) Patent No.: US 6,297,357 B1
(45) Date of Patent: Oct. 2, 2001

(54) PRB2/P130 PEPTIDE INHIBITORS OF CDK2 KINASE ACTIVITY

(75) Inventor: Antonio Giordano, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/130,425

(22) Filed: Aug. 6, 1998

Related U.S. Application Data
(60) Provisional application No. 60/056,207, filed on Aug. 21, 1997.

(51) Int. Cl.[7] .............................. C12P 12/04; C07K 1/00; C07H 21/02
(52) U.S. Cl. ................................ 530/350; 435/5; 435/7.2; 435/69.1; 435/69.7; 435/194; 530/350; 530/326; 930/220; 536/23.5
(58) Field of Search ...................................... 530/326, 550; 930/220; 536/23.5; 435/5, 7.2, 69.1, 69.7, 194

(56) References Cited

U.S. PATENT DOCUMENTS

| | | |
|---|---|---|
| 5,457,049 | 10/1995 | Giordano . |
| 5,496,731 | 3/1996 | Xu et al. . |
| 5,532,340 * | 7/1996 | Giordono . |
| 5,596,079 | 1/1997 | Smith et al. . |

FOREIGN PATENT DOCUMENTS

| | | |
|---|---|---|
| 0 666270 | 8/1995 | (EP) . |

OTHER PUBLICATIONS

Woo et al, Jul. 1997, Molecular and Cellular Biology,pp. 3566–3579 (entire document).*
Burgess et al. J. Cell. Biol. 111, 2129–2138, 1990.*
Lazar et al. Mol. Cell. biol. 8, 1247–1252, 1988.*
Tao et al. J. Immunol. 143, 2595–2601, 1989.*
Mayol et al. Oncogene, 8, 2561–2566, 1993.*
Li et al. Genes Dev. 7: 2366–77, 1933.*
Genbank database, Pir 60, AC No: I138150, Sep. 1996.*
Genbank database, Sptrembl 9, AC No: Q15073, Nov. 1996.*
Gu et al. Inhibition of CDK2 activity in vivo by an associated 20K regulatory subunit, 1993 Nature, 16 Dec., vol. 366: 707–710.
Claudio et al. "p130/pRb2 Has Growth Suppressive Properties Similar to Yet Distinctive from Those of Retinoblastoma Family Members pRb and P 107", 1994 Cancer Res. 54:5556–5560.
Baldi et al., "Genomic structur of the human retin0blastoma–related Rb2/p130gene", 1996 Pro. Natl. Acad. Sci. 93:4629–4632.

De Luca et a. A Unique Domain of pRb2/p130 Actas as an Inhibitor of Cdk2 Kinase Activity. The Journal of Biological Chemistry. Aug. 22, 1997, vol. 272, No. 34, pp 20971–20974, especially p. 20974, col. 2, first full paragraph.

Antelman et al., "Inhibition of tumor cell proliferation in vitro and in vivo by exogenous p110$^{RB}$, the retinoblastoma tumor suppressor protein", (1995) *Oncogene* 10:697–704.

Baldi et al., "The RB2/p130 Gene Product Is a Nuclear Protein Whose phosphorylation Is Cell Cycle Regulated", (1995) *J. Cell. Biochem.* 59:402–408.

Bookstein et al., "Suppression of Tumorigenicity of Human Prostate Carcinoma Cells by Replacing a Mutated RB Gene", (1990) *Science* 247:712–715.

Chellappan et al., "The E2F Transcription Factor Is a Cellular Target for the RB Protein", (1991) *Cell* 65:1053–61.

Claudio et al., "p130/pRb2 Has Growth Suppressive Properties Similar to yet Distinctive from those of Retinoblastoma Family Members pRb and p107[1]", (1994) *Cancer Res.* 54:5556–5560.

Elledge, S.J. and Spottswood, M.R., A new human p34 protein kinase, CDK2, identified by complementation of a cdc28 mutation in *Saccharomyces cerevisiae*, is a homolog of Xenpus Eg1 (1991) *EMBO J.* 10:2653–2659.

Ewen et al., "Molecular Cloning, Chromosomal Mapping, and Expression of the cDNA for p107, a Retinoblastoma Gene Product–Related Protein", (1991) *Cell* 66:1155–1164.

Ewen et al., "Interaction of –107 with Cyclin A Independent of Complex Formation with Viral Oncoproteins", (1992) *Science* 255:85–87.

Giordano et al., "Cell Cycle Regulation of Histone H1 Kinase Activity Associated with the Adenoviral Protein E1A", (1991) *Science* 253:1271–5.

Hannon et al., "Isolation of the Rb–related p130 through its interaction with CDK2 and cyclins", (1993) *Genes Dev.* 7:2378–91.

Hu et al., "The regions of the retinoblastoma protein needed for binding to adenovirus E1A or SV40 large T antigen are common sites for mutations", (1990) *EMBO J.* 9:1147–1155.

(List continued on next page.)

Primary Examiner—Geetha P. Bansal
Assistant Examiner—Mau Tran
(74) Attorney, Agent, or Firm—ReedSmith LLP; William J. McNichol, Jr.; Nanda P.B.A. Kumar

(57) ABSTRACT

The present invention provides peptides of pRb2/p130 or mutants or fragments thereof which inhibit cdk2 kinase activity. Method of inhibiting cdk2 kinase activity in cells with these peptides are also provided.

12 Claims, 1 Drawing Sheet

OTHER PUBLICATIONS

Huang et al., "Suppression of the Neoplastic Phenotype by Replacement of the RB Gene in Human Cancer Cells", (1988) *Science* 242:1563–1566.

Kamb et al., "A Cell Cycle Regulator Potentially Involved in Genesis of Many Tumor Types", (1994) *Science* 264:436–440.

Kiess et al., "Expression and Activity of the Retinoblastoma Protein (pRB)—Family Proteins, p107 and p130, during $L_6$ Myoblast", (1995) *Cell Growth Diff.* 6:1287–1298.

Lee et al., "The retinoblastoma susceptibility gene encodes a nuclear phosphoprotein associated with DNA binding activity", (1987) *Nature* 329:642–645.

Li et al., "The adenovirus E1A–associated 130–kD protein is encoded by a member of the retinoblastoma gene family and physically interacts with cyclins A and E", (1993) *Genes Dev.* 7:2366–77.

MacLaughlan et al., "Cyclins, Cyclin–Dependent Kinases and Cdk Inhibitors:Implications in Cell Cycle Control and Cancer", (1995) *Crit. Rev. in Eukary. Gene Ex.* 5:127–56.

Mayol et al., "Cloning of a new member of the retinoblastoma gene family (pRb2) which binds to the E1A transforming domain", (1993) *Oncogene* 8:2561–6.

Morgan et al., "Approaches to Discovery of Non–Peptide Ligands for Peptide Receptors and Peptidases", (1989) *Ann. Reports Med. Chem.* 24:243–252.

Nobori et al., "Deletions of the cyclin–dependent kinase–3 inhibitor gene in multiple human cancers", (1994) *Nature* 368:753–756.

Paggi et al., "Retinoblastoma Protein Family in Cell Cycle and Cancer: A Review", *J. Cell. Biochem.* (1996) 62:418–430.

Pines et al., "Isolation of a Human Cyclin cDNA: Evidence for Cyclin mRNA and Protein Regulation in the Cell Cycle and for Interaction with $p34^{cdc2}$", (1989) *Cell* 58:833–846.

Sherr, C.J. and Roberts, J.M., "Inhibitors of mammalian $G_1$ cyclin–dependent kinases", (1995) *Genes Dev.* 9:1149–63.

Xiong, Y., "Why are there so many CDK inhibitors?", (1996) *Biochim. Biophys. Act.* 1288:1–5.

\* cited by examiner

SEQUENCE LISTING

<160> NUMBER OF SEQ ID NOS: 3

<210> SEQ ID NO 1
<211> LENGTH: 213
<212> TYPE: PRT
<213> ORGANISM: Homo sapiens

<400> SEQUENCE: 1

```
Val Pro Thr Cys Glu Glu Val Met Pro Pro Gln Asn Leu Glu Arg Ala
 1               5                  10                  15

Asp Glu Ile Cys Ile Ala Gly Ser Pro Leu Thr Pro Arg Arg Val Thr
            20                  25                  30

Glu Val Arg Ala Asp Thr Gly Gly Leu Gly Arg Ser Ile Thr Ser Pro
        35                  40                  45

Thr Thr Leu Tyr Asp Arg Tyr Ser Ser Pro Pro Ala Ser Thr Thr Arg
    50                  55                  60

Arg Arg Leu Phe Val Glu Asn Asp Ser Pro Ser Asp Gly Gly Thr Pro
65                  70                  75                  80

Gly Arg Met Pro Pro Gln Pro Leu Val Asn Ala Val Pro Val Gln Asn
                85                  90                  95

Val Ser Gly Glu Thr Val Ser Val Thr Pro Val Pro Gly Gln Thr Leu
            100                 105                 110

Val Thr Met Ala Thr Ala Thr Val Thr Ala Asn Asn Gly Gln Thr Val
        115                 120                 125

Thr Ile Pro Val Gln Gly Ile Ala Asn Glu Asn Gly Gly Ile Thr Phe
    130                 135                 140

Phe Pro Val Gln Val Asn Val Gly Gly Gln Ala Gln Ala Val Thr Gly
145                 150                 155                 160

Ser Ile Gln Pro Leu Ser Ala Gln Ala Leu Ala Gly Ser Leu Ser Ser
                165                 170                 175

Gln Gln Val Thr Gly Thr Thr Leu Gln Val Pro Gly Gln Val Ala Ile
            180                 185                 190

Gln Gln Ile Ser Pro Gly Gly Gln Gln Lys Gln Gly Gln Ser Val
        195                 200                 205

Thr Ser Ser Ser Asn
    210
```

<210> SEQ ID NO 2
<211> LENGTH: 96
<212> TYPE: PRT
<213> ORGANISM: Homo sapiens

<400> SEQUENCE: 2

```
Pro Pro Ala Ser Thr Thr Arg Arg Arg Leu Phe Val Glu Asn Asp Ser
 1               5                  10                  15

Pro Ser Asp Gly Gly Thr Pro Gly Arg Met Pro Pro Gln Pro Leu Val
            20                  25                  30

Asn Ala Val Pro Val Gln Asn Val Ser Gly Glu Thr Val Ser Val Thr
        35                  40                  45

Pro Val Pro Gly Gln Thr Leu Val Thr Met Ala Thr Ala Thr Val Thr
    50                  55                  60

Ala Asn Asn Gly Gln Thr Val Thr Ile Pro Val Gln Gly Ile Ala Asn
65                  70                  75                  80

Glu Asn Gly Gly Ile Thr Phe Phe Pro Val Gln Val Asn Val Gly Gly
                85                  90                  95
```

<210> SEQ ID NO 3
<211> LENGTH: 71
<212> TYPE: PRT
<213> ORGANISM: Homo sapiens

<400> SEQUENCE: 3

```
Met Pro Pro Gln Pro Leu Val Asn Ala Val Pro Val Gln Asn Val Ser
 1               5                  10                  15

Gly Glu Thr Val Ser Val Thr Pro Val Pro Gly Gln Thr Leu Val Thr
            20                  25                  30

Met Ala Thr Ala Thr Val Thr Ala Asn Asn Gly Gln Thr Val Thr Ile
        35                  40                  45

Pro Val Gln Gly Ile Ala Asn Glu Asn Gly Gly Ile Thr Phe Phe Pro
    50                  55                  60

Val Gln Val Asn Val Gly Gly
65                  70
```

PRB2/P130 PEPTIDE INHIBITORS OF CDK2 KINASE ACTIVITY

This application claims the benefit of U.S. Provisional Application 60/056,207, filed Aug. 21, 1997.

INTRODUCTION

This invention was made in the course of research sponsored by the National Institutes of Health. The U.S. Government may have certain rights in this invention.

BACKGROUND OF THE INVENTION

Over the past years, unscheduled mitosis has been considered to be a major characteristic of either benign or malignant neoplastic disease. Cancer development is believed to be due to a loss of control in the cellular strategies that regulate the cell cycle.

The mammalian cell cycle is believed to be driven by the sequential activation and deactivation of various cyclin/cyclin-dependent kinase (cdk) pairs (MacLachlan et al. (1995) *Crit. Rev. in Eukary. Gene Ex.* 5:127–56). The prototypic cell cycle kinase, cdc2, was originally discovered in yeast and found to be involved in regulating both DNA replication and mitosis. Higher organisms, however, were found to possess a more complex system monitoring these events.

One of several kinases involved, cyclin dependent kinase 2 (cdk2), is necessary for mammalian cells to pass the restriction point and onto DNA replication (Elledge, S. J. and Spottswood, M. R. (1991) *EMBO J.* 10:2653–2659). Activation and deactivation of this kinase is critical to the precise timing of the onset of S phase, after which a cell is committed to divide. Temporal association with cyclins A or E depict when the kinase will be active, and therefore phosphorylates the substrates involved in DNA replication. Over the last few years, several mechanisms besides cyclin binding have been discovered that control cdk activity. In addition to differences in phosphorylation status and cofactor binding, a growing number of low molecular weight proteins are now known to bind to and inhibit cdk kinase activity (Xiong, Y. (1996) *Biochim. Biophys. Act.* 1288:1–5; Sherr, C. J. and Roberts, J. M. (1995) *Genes Dev.* 9:1149–63). The CIP/KIP family (p21, p27, p57) and the INK family (p15, p16, p18, p19) of cdk inhibitors bind either the cyclin or directly to the cdk and suppress its kinase activities until cell cycle progression may continue. The INK family have a specificity for the early G1 kinases cdk4 and cdk6 complexed with D-type cyclins, while the CIP family is partial to cdk2 bound to either cyclin A or E. When overexpressed in a variety of cell types, these inhibitors are able to halt growth and arrest the cells in G1 phase. Accordingly, these are temporally regulated proteins, with a preference for potently inhibiting G1 cyclin-cdk pairs. The loss of several of these proteins has been found to be a critical step in oncogenesis. For example, the p16 and p15 genes both lie in a region found deleted in some 75% of all melanoma cases (Kamb et al. (1994) *Science* 264:436–440; Nobori et al. (1994) *Nature* 368:753–756). It appears that cdk inhibition is essential for normal cell cycle progression.

The retinoblastoma family consists of a group of genes, the proteins of which are also involved in eukaryotic cell cycle homeostasis. Proteins encoded by these genes are often referred to as "pocket proteins" due to their unique tridimensional structure. This structure is responsible for most of the specific and functionally relevant protein-protein interactions in which these molecules are involved. At present, the family consists of three members including the retinoblastoma (RB) gene which codifies a protein called pRb, p107 which codifies a protein called p107, and p130, also referred to as pRb2/p130, which codifies a protein called pRb2/p130.

All three pocket proteins are localized mainly in he nuclear compartment of the cells (Lee et al. (1987) *Nature* 329:642–645; Ewen et al. (1991) *Cell* 66:1155–1164; Baldi et al. (1995) *J. Cell. Biochem.* 59:402–408). Each protein structure consists basically of an N-terminal portion, the pocket structure subdivided into domain A, spacer and domain B, and a C-terminal portions, also called domain C. The pocket functional domains A and B are the most conserved and have been taught to responsible for most of the interactions involving either endogenous proteins or viral oncoproteins (Paggi et al. *J. Cell. Biochem.* (1996) 62:418–430).

The Rb protein is most well known for its interaction with and inhibition of the E2F transcription factor. It is believed that E2F is able to transactivate several genes whose products are necessary for DNA replication to occur. However, when bound to pRb, this transactivating ability is lost (Chellappan et al. (1991) *Cell* 65:1053–61). pRb is also found lost in several types of cancers, including retinoblastoma. The Rb related proteins p107 and pRb2/p130 have been found to have similar, yet distinctive qualities from pRb (Ewen et al. (1991) *Cell* 66:1155–64; Mayol et al. (1993) *Oncogene* 8:2561–6; Li et al. (1993) *Genes Dev.* 7:2366–77; and Hannon et al. (1993) *Genes Dev.* 7:2378–91). While pRb, p107, or pRb2/p130 overexpression can drive cancer cells to growth inhibition or arrest (Huang et al. (1988) *Science* 242:1563–1566; Bookstein et al. (1990) *Science* 247:712–715; Antelman et al. (1995) *Oncogene* 10:697–704; and Claudio et al. (1994) *Cancer Res.* 54:5556–5560), certain tumor cells are not equally responsive to any pocket protein. For example, the SAOS-2 human osteosarcoma cell line, which possesses a truncated non-functional pRb molecule is definitely sensitive to pRb and p107 growth suppressive properties. On the other hand, while pRb2/p130 overexpression slows down SAOS-2 growth, this protein has also been able to inhibit proliferation in the T98G human glioblastoma multiform and in the MCF-7 human mammary adenocarcinoma cell lines, while neither pRb nor p107 showed any inhibitory effect. Both T98G and MCF-7 cell lines display homozygous deletion of the p16 $^{INK4A}$ gene, a cdk4 and cdk6 inhibitor. Accordingly, is has been suggested that pocket protein Rb and p107 are become extensively phosphorylated by specific cyclin/cdk complexes, thus becoming functionally inactive in blocking the cell cycle. It is believed, however, that pRb2/p130 which has been found to be coupled to cdk2 is able to overcome $p16^{INK4A}$ homozygous deletion, bringing about effective growth inhibition in these cell lines (Paggi et al. *J. Cell. Biochem.* (1996) 62:418–430).

The functional domain of the Rb and p107 proteins have been mapped through both genetic and biochemical means (Hu et al. (1990) *EMBO J.* 9:1147–1155; Ewen et al. (1991) *Cell* 66:1155–1164; Ewen et al. (1992) *Science* 255:85–87). An approximately 400 amino acid fragment of Rb and p107, termed the Rb pocket, is responsible for association of these proteins with the DNA tumor virus oncoproteins and cellular ligands. Within this domain are six regions of extensive sequence similarity. Similarly, the cyclins share a large region of sequence similarity spanning approximately 87 amino acids which has been designated that the "cyclin box" (Pines et al. (1989) *Cell* 58:833–846). This domain is believed to be important in Rb and p107 protein:protein interactions. In fact peptides having sequences comprising a portion of this domain have been proposed as inhibitors of cell growth and proliferation (U.S. Pat. No. 5,625,031).

It has now been found that the inhibitory activity of the related Rb protein, pRb2/p130, occurs not through this cyclin box, but rather through a different and separate domain of the spacer region. Further, increased expression of pRb2/p130 during various cellular processes was demonstrated to be associated with decreased kinase activity of cdk2. For example, pRb2/p130 protein levels are increased upon differentiation of myocytes, coincident with cdk2 kinase inhibition. This is quite different from the related p107 protein, levels of which have been shown to decrease. Accordingly, it is believed that pRb2/p130 acts not only to bind and modify E2F activity, but also to inhibit cdk2 kinase activity in concert with p21 in a manner different from other Rb proteins.

SUMMARY OF THE INVENTION

An object of the present invention is to provide peptides comprising amino acids 641 to 711 of pRb2/p130 or fragments, mutants or homologous amino acid sequences thereof which inhibit cdk2 kinase activity.

Another object of the present invention is to provide a method of inhibiting cdk2 kinase activity which comprises contacting cells with a peptide comprising amino acids 641 to 711 of pRb2/p130 or fragments, mutants or homologous amino acid sequences thereof which inhibits cdk2 kinase activity.

DETAILED DESCRIPTION OF THE INVENTION

Figure 1:
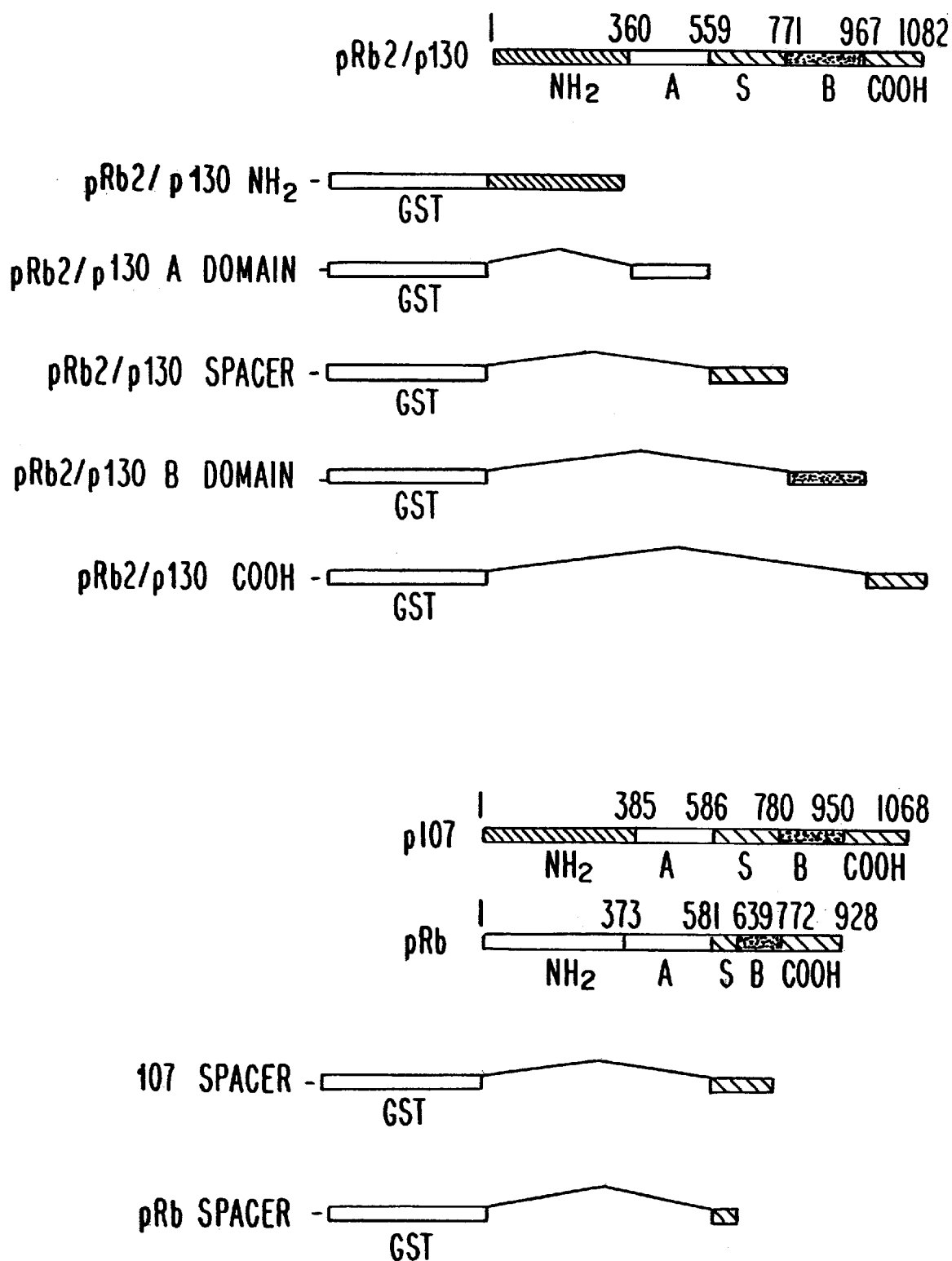
FIG. 1 provides a schematic representation of the glutathione S-Transferase-pRb, p107 and pRb2/p130 fusion proteins.

Cancer is a group of heterogeneous pathologic states in which cells lose the control of proliferation, and as a consequence, increase in abundance abnormally and invade surrounding tissues. It is usually characterized by rapid, uncontrolled cell division, increased cell survival ability and accompanied by de-differentiation and accumulation of genetic alterations. Uncontrollable cell division may not only increase cell numbers, but also contribute to the accumulation of genetic alterations, a common phenomenon found in cancer cells. The accumulating alterations may further deteriorate the impaired cell cycle control mechanism.

cdk2, an important regulator of the human cell cycle, has been mapped on chromosome 12q13. This locus has been shown to be frequently altered or translocated in a number of tumors including, but not limited to, uterine leiomyoma, adenoma of the salivary gland and human acute myeloblastic leukemia. Alterations of the 12q13 locus in tumors are believed to involve changes in the regulation of the cdk2 gene. More specifically, activity of the cdk2 protein is increased resulting in proliferation of the tumor cells. Accordingly, identifying compounds that inhibit cdk2 activity would be useful in the regulation and control of the proliferating cancer cells.

Because of their ability to interact with the cell cycle control machinery and their growth suppressive effects, pocket proteins have been considered for use in control of neoplastic growth (Paggi et al. *J. Cell. Biochem.* (1996) 62:418–430). The pRb2/p130 gene product is a nuclear protein whose phosphorylation is cell cycle regulated (Baldi et al. (1995) *Journal of Cellular Biochemistry* 59:402–408). Based upon the association with the G0 specific transcription factor E2F5 and high expression in differentiated or quiescent cells, it has been suggested that pRb2/p130 acts primarily in early G1 phase. In addition to potential modification of E2F protein functions, pRb2/p130 has now been found to contribute to G0/G1 arrest by decreasing the activity of kinases such as cdk2, that allow the cell to enter S phase.

While the highly homologous p107 protein has also been shown to have this effect on cdk2, the effects of pRb2/p130 on cdk2 differ in several respects. For example, when p107 is added in increasing amounts to cdk2 kinase assays, pRb and histone H1 substrates decrease in phosphorylation, while p107 itself becomes increasingly phosphorylated. This suggests that p107 acts more like a preferential substrate, not an inhibitor. In contrast, pRb2/p130 does not become phosphorylated in in vitro assays, and therefore does not act as an alternative substrate, but rather as a binding protein with inhibitory properties. Further, it has been taught that p107 may not act so much as an cdk inhibitor, but rather masks cdk2/cyclin A from its substrate, E2F4. In contrast, in model in vivo systems, pRb2/p130 protein increases are coincident with cdk2 inhibition, suggesting that pRb2/p130 may not only act to regulate E2F activity, but also kinase activity as well.

The region of pRb2/p130 that displays the greatest inhibitory effect is one that is poorly conserved between the two proteins. It is believed that this region of low homology may be responsible for the functional divergence of proteins in the Rb family. A unique domain of the pRb2/p130 protein has now been identified which is capable of inhibiting cdk2 kinase activity in vitro. This domain is very close to the predicted E2F binding site and the C-terminus.

Several models have suggested that there is an inverse relationship between pRb2/p130 protein concentration and cdk activity. For example, ML1 myeloma cells, when undergoing differentiation in vitro, show a marked increase in pRb2/p130 protein by terminal differentiation, while associated cdk2 kinase activity decreases to basal levels. The murine hematopoietic progenitor cell line FDC-P1 also displays a high amount of pRb2/p130 in early G1 phase which is coupled with a decrease in associated cdk2 histone H1 kinase activity. As protein levels decline in late G1, kinase activity is restored to cdk2.

The relationship of pRb2/p130 protein concentrations and cdk2 activity was examined in the myoblast cell line, C2C12. When cultured in medium containing 2% horse serum, C2C12 cells undergo cell cycle arrest, fuse with neighboring cells and elongate into fully differentiated, multinucleated muscle fibers. After 5 days in this differentiation medium, cells had obtained a complete myotubular morphology. Previous studies have shown that p107 protein decreases during muscle differentiation (Kiess et al. (1995) *Cell Growth Diff.* 6:1287–1298). In contrast, immunoblotting of protein extracts from 24 hour time points of these cells showed an increase of more than twice the amount of pRb2/p130 protein. pb2/p130 complexes were also immunoprecipitated from these extracts and subjected to a kinase assay using Histone H1 as substrate to assess associated cdk2 activity. cdk2 kinase activity decreased more than half by the end of the differentiation pathway. Protein levels of cdk2 were confirmed to be equal in all samples which underwent kinase analysis. These results taken together show concomitantly that as pRb2/p130 protein levels increase, associated cdk2 activity decreases, suggesting that pRb2/p130 may play a role in inhibiting the activity of this kinase. Further, pRb2/p130 appears to differ in its functional similarities with p107 with respect to binding cell cycle machinery.

Since there is a correlation of pRb2/p130 protein levels and cdk2 kinase activity, the ability of pRb2/p130, to directly inhibit cdk2 was determined. A panel of mutants, representing different regions of pRb2/p130 and p107 and pRb as controls, were developed and expressed as GST fusion proteins (see FIG. 1). cdk2 complexes were immunoprecipitated from lysates of exponentially growing ML1 myeloma cells. Twenty micrograms of a GST-fusion protein was then added to the precipitates and the mixtures were subjected to a kinase assay using histone H1 as substrate. The A and B domains of the pocket and C-terminal regions of pRb2/p130 had little or no effect on the kinase activity of cdk2 compared to precipitates treated with GST alone, while the N terminus had moderate inhibitory activity. However, the spacer region, whose amino acid sequence is specific to pRb2/p130, decreased cdk2-dependent histone phosphorylation significantly. Further, the inhibitory effect of the spacer regions on cdk2 activity was found to be dose dependent.

The inhibitory activity of the spacer region is also unique to pRb2/p130. Experiments were performed wherein spacer regions from all Rb protein family members were expressed as GST fusion proteins and added in large excess to kinase assays of cdk2. However, only pRb2/p130 was able to inhibit cdk2 kinase activity significantly through this region.

The specificity of this spacer region for cdk2 was confirmed. In these experiments, cdc2-family members including cdc2, cdk2, cdk4 and cdk5 were immunoprecipitated from ML1 cells and were subjected to a kinase assay using either histone H1 or Rb as substrate. The spacer region of pRb2/p130 was only able to decrease cdk2 kinase activity, demonstrating that the inhibitory activity associated with pRb2/p130 is specific for the kinase it is able to bind stably in cells, cdk2.

The region demonstrated to inhibit the activity of cdk2 comprises a portion of the spacer region of pRb2/p130 corresponding to amino acids 559 to 771 (SEQ ID NO: 1). Further experiments have identified peptides comprising amino acids 616 to 711 (SEQ ID NO: 2) and amino acids 641 through 711 (SEQ ID NO: 3) to retain this inhibitory effect. Peptides consisting of amino acids 616 to 642, 641 to 666, 663 to 711, and 616 to 666 did not retain an inhibitory effect. Accordingly, for the purposes of the present invention, by "peptide" it is meant to include peptides comprising SEQ ID NO: 1, SEQ ID NO: 2, or SEQ ID NO: 3 or fragments or mutants thereof and homologous amino acid sequences having similar cdk2 inhibitory activity. Homologous amino acid sequences are sequences having at least about 85%, and preferably 90–95% of the amino acids match over a defined length of the peptide determined to have cdk2 inhibitory activity. By "peptide" it is also meant to include peptide mimetics which are structures which serve as substitutes for peptides in interactions with acceptor molecules (see Morgan et al. (1989) *Ann. Reports Med. Chem.* 24:243–252 for a review of peptide mimetics). Peptide mimetics include, but are not limited to synthetic structures which may or may not contain amino acids and/or peptide bonds, but retain the structural and functional features of a peptides ligand. Also included within this term are peptoids and oligopeptoids which are peptides or oligomers of N-substituted amino acids. By peptide mimetics it is also meant to include peptide libraries which are collections of peptides designed to be specified amino acid length and representing all conceivable sequences of amino acids corresponding thereto. Methods of generating peptide libraries are well known to those of skill in the art.

Peptides of the present invention which are capable of exhibiting this inhibitory activity can be defined by generating deletion mutants beginning at the COOH terminus of the full length protein. Chimeric fusion proteins corresponding to these mutant sequences are then generated in accordance with Examples 1 and 2 using the PGEX-2T expression vector system. Peptide sequences of pRb2/p130 which retain inhibitory activity can then be prepared synthetically in accordance with well known methods such as solid or solution phase peptide synthesis. Alternatively, peptides of the present invention may be synthesized recombinantly. Assays used to characterize peptides of the present invention are described in Example 4.

Peptides of the present invention which inhibit cdk2 activity will be useful in inhibiting the cell proliferation progression through the G1/S phases of the cell cycle by physically preventing the activation of cdk2. These peptides, which control cell cycle progression by inhibiting the kinase activity of cdk2, are expected to lead to a halt in tumor growth. The stage of progression and/or type of malignancy will dictate the amount and route of administration of peptide needed to produce an effect.

In addition, these peptides will be useful in studying the normal function of cdk2 in the regulation of the G1/S phases of the cell cycle.

The following nonlimiting examples are provided to further illustrate the present invention.

EXAMPLES

Example 1

Construct Preparation

A prokaryotic expression vector pGEX-2T (Stratagene, La Jolla, Calif.) and the polymerase chain reaction (PCR) were used to generate chimeric glutathione S-transferase. The primers used to amplify the PCR fragments that were subcloned in the pGEX-2T were derived from the 5' and 3' ends of the $NH_2$, A, Spacer, B and COOH domain of pRb2/p130 and the Spacer domain of pRb and p107. The pGEX-2T fusion proteins generated are shown in FIG. 1.

Example 2

GST Fusion Protein Preparation

XL1-Blue bacteria carrying pGEX-2T vectors were grown to mid log phase and then induced to express protein by the addition of IPTG to the media to a concentration of 0.25 mM. The cultures were then shaken for four hours. Bacteria were then pelleted and resuspended in NENT buffer (20 mM Tris pH 8, 100 mM NaCl, 1 mM EDTA, 0.5% NP 40). Cell suspensions were sonicated, pelleted and the supernatant collected. The remaining bacteria were then resuspended in NENT+2% N-Lauryl-Sarcosine, pelleted and the supernatant was again collected. The combined supernatants were incubated with Glutathione agarose (Pharmacia, Piscataway, N.J.) overnight at 4° C. The agarose was then pelleted and washed three times in NENT buffer.

Example 3

Immuno Blotting

Cell lysates were prepared by resuspending pelleted cells in 200 µl lysis buffer (50 mM Tris, 5 mM EDTA, 250 mM NaCl, 50 mM NaF, 0.1% Triton, 0.1 mM Na$_3$VO$_4$, plus protease inhibitors). Fifty micrograms of protein were run on a 7% polyacrylamide gel. Proteins within the polyacrylamide gel were transferred to a PVDF membrane (Millipore Corp., Bedford, Mass.) in CAPS buffer (10 mM CAPS, 20% methanol, pH 11). The membrane was blocked with 5% milk in TBS-T buffer (2 mM Tris, 13.7 mM NaCl, 0.1% Tween-20, pH 7.6) and then washed in TBS-T. Primary antibody was incubated with the membrane in 3% milk and then washed in TBS-T. The membrane was then incubated with anti-rabbit Ig coupled with horseradish peroxidase (Amersham, Arlington Hts, Ill.) and washed in TBS-T. The presence of secondary antibody bound to the membrane was detected using the ECL system (Dupont NEN, Boston, Mass.).

Example 4

Kinase Assays

Cell lysates were prepared by resuspending pelleted cells in 200 μl lysis buffer (50 mM Tris, 5 mM EDTA, 250 mM NaCl, 50 mM NaF, 0.1% Triton, 0.1 mM Na$_3$VO$_4$, plus protease inhibitors). An equal amount of protein for each fraction was immunoprecipitated with a specific Ab. Prior to detecting the presence of Histone H1 kinase activity, each sample was incubated with an equal amount of the PGEX-2T constructs previously described for 30 minutes at 4° C. Protein kinase assays were performed in accordance with procedures described by Giordano et al. (1991) *Science* 253:1271–5. Kinase assays were repeated at least three times giving an interassay standard deviation within 10% after normalization for protein amount.

What is claimed is:

1. An isolated cdk2 kinase activity inhibiting polypeptide consisting essentially of SEQ ID NO: 3.

2. An isolated cdk2 kinase activity inhibiting polypeptide consisting essentially of the amino acid sequence of SEQ ID NO: 1 or having 95% identity to the amino acid sequence of SEQ ID NO: 1 over the full length of SEQ ID NO: 1.

3. The isolated cdk2 kinase activity inhibiting polypeptide of claim 2, wherein the isolated polypeptide consist essentially of the amino acid sequence of SEQ ID NO: 1.

4. The isolated cdk2 kinase activity inhibiting polypeptide of claim 2, wherein the isolated polypeptide has 95% identity to the amino acid sequence of SEQ ID NO: 1 over the full length of SEQ ID NO: 1.

5. An isolated cdk2 kinase activity inhibiting polypeptide consisting essentially of the amino acid sequence of SEQ ID NO: 2 or having 95% identity to the amino acid sequence of SEQ ID NO: 2 over the full length of SEQ ID NO: 2.

6. The isolated cdk2 kinase activity inhibiting polypeptide of claim 5, wherein the isolated polypeptide consist essentially of the amino acid sequence of SEQ ID NO: 2.

7. The isolated cdk2 kinase activity inhibiting polypeptide of claim 5, wherein the isolated polypeptide has 95% identity to the amino acid sequence of SEQ ID NO: 2 over the full length of SEQ ID NO: 2.

8. An isolated cdk2 kinase activity inhibiting polypeptide consisting essentially of the amino acid sequence of SEQ ID NO: 1, 2 or 3 that is fused to a second polypeptide.

9. The isolated cdk2 kinase activity inhibiting polypeptide of claim 8, wherein the fusion polypeptide consist essentially of the amino acid sequence of SEQ ID NO: 1.

10. The isolated cdk2 kinase activity inhibiting fusion polypeptide of claim 8, wherein the fusion polypeptide consist essentially of the amino acid sequence of SEQ ID NO: 2.

11. The isolated cdk2 kinase activity inhibiting fusion polypeptide of claim 8, wherein the fusion polypeptide consist essentially of the amino acid sequence of SEQ ID NO: 3.

12. The isolated cdk2 kinase activity inhibiting fusion polypeptide of claim 8, wherein the second polypeptide is glutathione S-transferase.

* * * * *